US010357171B2

(12) United States Patent
Virtanen

(10) Patent No.: US 10,357,171 B2
(45) Date of Patent: Jul. 23, 2019

(54) ADJUSTABLE ECG SENSOR AND RELATED METHOD

(71) Applicant: General Electric Company, Schenectady, NY (US)

(72) Inventor: Juha Petri Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 307 days.

(21) Appl. No.: 15/205,371

(22) Filed: Jul. 8, 2016

(65) Prior Publication Data

US 2018/0008160 A1 Jan. 11, 2018

(51) Int. Cl.
*A61B 5/0408* (2006.01)
*A61B 5/0432* (2006.01)
*A61B 5/00* (2006.01)
*G06F 19/00* (2018.01)
*G16H 40/67* (2018.01)

(52) U.S. Cl.
CPC .......... *A61B 5/0408* (2013.01); *A61B 5/0022* (2013.01); *A61B 5/0432* (2013.01); *A61B 5/6832* (2013.01); *A61B 5/6838* (2013.01); *G06F 19/00* (2013.01); *G16H 40/67* (2018.01)

(58) Field of Classification Search
CPC .......................... A61B 5/0408; A61B 5/04286
See application file for complete search history.

(56) References Cited

U.S. PATENT DOCUMENTS

| 4,815,964 | A | * | 3/1989 | Cohen | ................. | A61B 5/0408 |
|           |   |   |        |       |                   | 600/392     |
| 5,341,806 | A | * | 8/1994 | Gadsby | ............. | A61B 5/04085 |
|           |   |   |        |       |                   | 600/391     |
| 6,496,705 | B1 |  | 12/2002 | Ng et al. | | |
| 6,749,566 | B2 |  | 6/2004 | Russ | | |

(Continued)

FOREIGN PATENT DOCUMENTS

| EP | 1359842 B1 | 5/2009 |
| EP | 2559280 A1 | 2/2013 |

(Continued)

OTHER PUBLICATIONS

Pending U.S. Appl. No. 14/586,393, filed Dec. 30, 2014, "Common Display Unit for a Plurality of Cableless Medical Sensors", Muuranto.

(Continued)

*Primary Examiner* — Lee S Cohen
(74) *Attorney, Agent, or Firm* — Andrus Intellectual Property Law, LLP

(57) ABSTRACT

An adjustable ECG sensor is attachable to a patient to sense cardiac signals and includes an adjustable leadwire having a flexible substrate, a conductor extending along the flexible substrate, and a connector end connectable to a receiver associated with an ECG monitor. The adjustable ECG sensor further includes an electrode having an electrode pad, a clip connected to the electrode pad and attachable to any one of multiple locations on the adjustable leadwire, and a pin that punctures the flexible substrate and electrically connects to the conductor of the adjustable leadwire. The adjustable (Continued)

ECG sensor is fitted to the patient by attaching the clip of the electrode to one of the multiple locations on the adjustable leadwire.

15 Claims, 6 Drawing Sheets

(56) References Cited

U.S. PATENT DOCUMENTS

| | | | |
|---|---|---|---|
| 7,390,299 B2 | 6/2008 | Weiner et al. | |
| 8,475,368 B2 | 7/2013 | Tran et al. | |
| 2004/0019288 A1* | 1/2004 | Kinast | A61B 5/0402 600/509 |
| 2004/0173003 A1 | 9/2004 | Ibane | |
| 2006/0136768 A1 | 6/2006 | Liu et al. | |
| 2006/0284621 A1 | 12/2006 | Doi | |
| 2008/0284599 A1 | 11/2008 | Zdeblick | |
| 2009/0318818 A1 | 12/2009 | Whitaker et al. | |
| 2010/0168605 A1 | 7/2010 | Aarts | |
| 2011/0066051 A1 | 3/2011 | Moon | |
| 2011/0145894 A1 | 6/2011 | Morchon et al. | |
| 2012/0068855 A1 | 3/2012 | Matsumura | |
| 2012/0108917 A1 | 5/2012 | Libbus et al. | |
| 2013/0053674 A1 | 2/2013 | Volker | |
| 2013/0109927 A1 | 5/2013 | Menzel | |
| 2013/0337842 A1 | 12/2013 | Wang et al. | |
| 2014/0180054 A1* | 6/2014 | Tremblay | A61B 5/04085 600/382 |
| 2014/0187883 A1 | 7/2014 | Lisogurski | |
| 2015/0116130 A1 | 4/2015 | Grubis | |
| 2017/0319093 A1* | 11/2017 | Stewart | A61B 5/04001 |

FOREIGN PATENT DOCUMENTS

| | | |
|---|---|---|
| EP | 1881784 B1 | 10/2013 |
| WO | 2014027273 A1 | 2/2014 |

OTHER PUBLICATIONS

Radius-7 brochure, Masimo, admitted prior art.
IntelliVue Cableless Measurement brochure, Philips, Jun. 2013.

* cited by examiner

ADJUSTABLE ECG SENSOR AND RELATED METHOD

BACKGROUND

This disclosure generally relates to medical monitoring systems and devices, and more specifically to ECG sensors and a method of using the same.

Electrocardiograms (ECGs) are graphic depictions of electrical activity in the heart. ECGs are produced by electrocardiographs which are available as stand alone devices, portable devices, and/or as integrated functions in various types of multi-vital sign monitoring devices. Typically, ECGs are used as diagnostic tools in various settings, such as hospitals and doctor's offices. ECGs comprise ECG waveforms for each of various leads, which are calculated based on cardiac signals recorded from electrodes attached to the patient. Various ECG recording methods are widely employed using various electrode configurations. To provide just a few examples, 3-lead ECG employing a three electrode arrangement, 5-lead ECG employing a five electrode arrangement, and a 12-lead ECG employing a ten electrode arrangement are all well known in the relevant field, along with other known electrode arrangements. Color coding standards for particular electrode locations are employed so that the electrodes can be visually differentiated, such as the color coding standard developed by the American Heart Association (AHA) and the color coding standard developed by the International Electrotechnical Commission (IEC).

ECGs are depicted by time (ms) versus voltage (mV) and typically are represented as a waveform. The typical five important aspects, or portions, of an ECG waveform are the P wave, QRS complex (represented as the combination of the Q, R, and S waves respectively), and T wave. The less frequently seen sixth portion is a U wave. The data produced from the graphical depictions are useful in diagnosis of patients to determine what, if any, and the extent to which heart-related problems exist in a patient. For instance, ECGs are used in diagnosing: cardiac arrhythmias (irregular heart rhythms), myocardial infarction (heart attacks), hyper- and hypokalemia (high or low potassium levels, respectively), blockage, ischemia (loss of oxygen due to lack of blood flow possibly from blockage), just to name a few, and may also assist in diagnosis of non-heart related ailments. Accordingly, ECGs are known and proven to be valuable tools in diagnosis heart and even non-heart-related problems with patients.

Particularly, the ECG waveforms are useful in determining whether certain conditions exist or the predisposition of such conditions occurring based on established patterns. Particularly, important information can be derived by measuring the time between certain waveforms; commonly reviewed time intervals are those between the P wave and the beginning of the QRS interval (known as the PR interval) and the time between the QRS complex and the T wave (known as the QT interval. Other relevant data may be derived from the PR segment, the QRS complex, and the ST segment.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an adjustable ECG sensor is attachable to a patient to sense cardiac signals and includes an adjustable leadwire having a flexible substrate, a conductor extending along the flexible substrate, and a connector end connectable to a receiver associated with an ECG monitor. The adjustable ECG sensor further includes an electrode having an electrode pad, a clip connected to the electrode pad and attachable to any one of multiple locations on the adjustable leadwire, and a pin that punctures the flexible substrate and electrically connects to the conductor of the adjustable leadwire. The adjustable ECG sensor is fitted to the patient by attaching the clip of the electrode to one of the multiple locations on the adjustable leadwire.

One embodiment of an adjustable leadwire set includes two or more adjustable leadwires, each adjustable leadwire having: an initial length of a flexible substrate having a flat top surface and a flat bottom surface; a conductor comprised of conductive ink printed on the top surface of the flexible substrate; an insulating layer over the top surface of the flexible substrate and the conductor; an adhesive on the bottom surface of the flexible substrate; and a connector end connected to each of the two or more adjustable leadwires and connectable to a receiver associated with an ECG monitor. Each adjustable leadwire is configured to connect to an electrode at any one of multiple locations along the initial length.

In one embodiment, a method of fitting an adjustable ECG sensor to a patient to sense cardiac signals includes adhering an electrode to a patient, the electrode having an electrode pad, a clip connected to the electrode pad, and a pin. The method further includes fitting an adjustable leadwire to the patient—the adjustable leadwire having an initial length of a flexible substrate having a connector end and a distal end, a conductor extending along the flexible substrate, and an adhesive on one side of the flexible substrate—by: adhering the adjustable leadwire to the patient; attaching the clip to any one of multiple locations on the adjustable leadwire; puncturing the flexible substrate with the pin to electrically connect to the conductor of the adjustable leadwire at a connection point; and severing the adjustable leadwire between the distal end and the connection point.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Currently available ECG monitoring systems and methods typically includes one-size-fits-all ECG sensors having an electrode at the end of a long leadwire. Since only one size leadwire is provided, they are designed to accommodate worst case scenario situations where long leadwires are required, and thus the leadwires often are much longer than necessary. The excessively long leadwires often hinder patient movement, as patient movement often results in entanglement in the leadwires and dislodging one of the electrodes. Excessively long leadwires are also problematic for the nursing staff, because the leadwires get easily detached from the electrodes during care operations, such as turning the patient or rearranging the protective sheets on a patient in an operating room setting. Furthermore, excessively long leadwires can lead to the introduction of unnecessary noise into the recorded signals.

In view of the foregoing problems and challenges with currently available ECG sensors and monitoring systems, the inventor developed the adjustable ECG sensors and leadwire sets, and related methods, disclosed herein. Specifically, the present inventors endeavored to develop an ECG sensor having an adjustable leadwire, where the leadwire can be sized to fit exactly to an arrangement of electrodes assembled on a patient, thereby eliminating entanglement problems, excess noise, etc. As disclosed herein, one embodiment of the disclosed adjustable leadwires has an adhesive on one side of the leadwires to allow the leadwires to be adhered to the patient's skin, further alleviating the leadwire entanglement problems described above.

Figure 1:
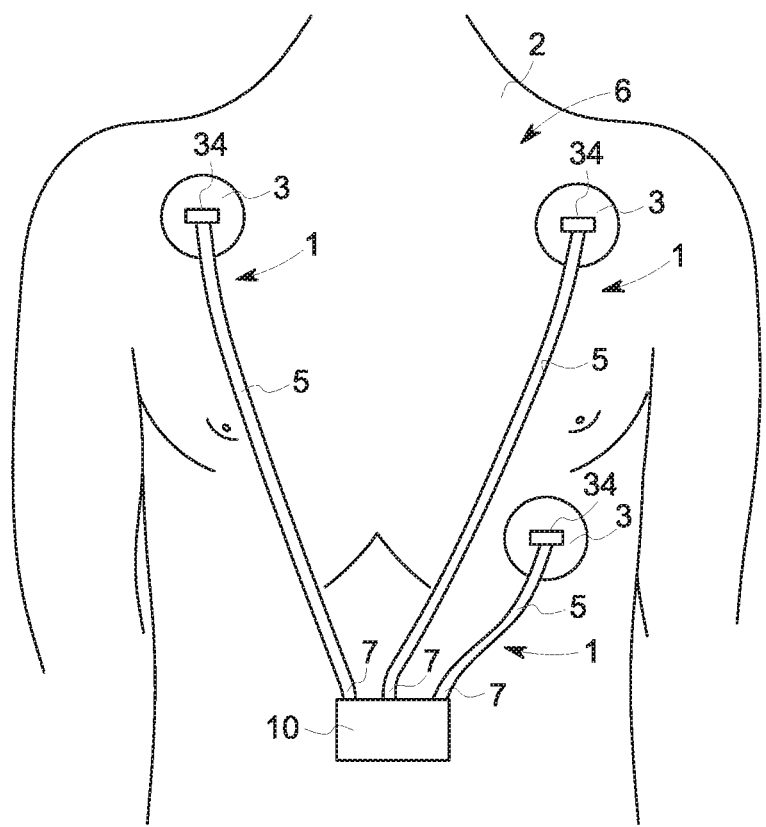
FIG. 1 depicts one embodiment of adjustable ECG sensors on a patient.

FIG. 1 depicts one embodiment of adjustable ECG sensors 1 on a patient 2 for obtaining a 3-lead ECG. While the depicted embodiment includes 3 adjustable ECG sensors 1, such arrangement is for the purposes of example only. A person having ordinary skill in the art will understand in light of the disclosure that any number of adjustable ECG sensors 1 may be employed in various arrangement in order to record ECGs including various numbers of leads. The adjustable ECG sensors 1 each comprise an adjustable leadwire 5 connected to an electrode 3 via a clip 34 on the electrode 3. In the depicted embodiment, the adjustable leadwires 5 form a leadwire set 6, each having a connector end 7 at a common connector 10 that wirelessly communicates with a receiver 15b associated with an ECG monitor 17 (see FIG. 5). Each of the adjustable ECG sensors 1 has been sized to fit the electrode 3 arrangement on the patient—i.e., to connect between the common connector 10 and the respective electrode 3—and thus the adjustable leadwires 5 fit perfectly to the patient with no excess leadwire posing an entanglement hazard. Further, in certain embodiments, the adjustable leadwires 5 are each adhered to the patient's skin, such as along the length of the leadwire, which holds the adjustable leadwire 5 snugly to the patient's chest and further avoids any potential for entanglement.

In one embodiment, the common connector 10 may be provided with adhesive or other means (such as a band, strap, or necklace) for fixing or connecting the common connector 10 to the patient's skin. FIG. 1 depicts such an embodiment, where the common connector 10 is adhered to the torso of the patient 2. Thereby, the adjustable ECG sensors 1 remain secured to the patient's torso and the problems of entanglement are entirely avoided.

Figure 2A:
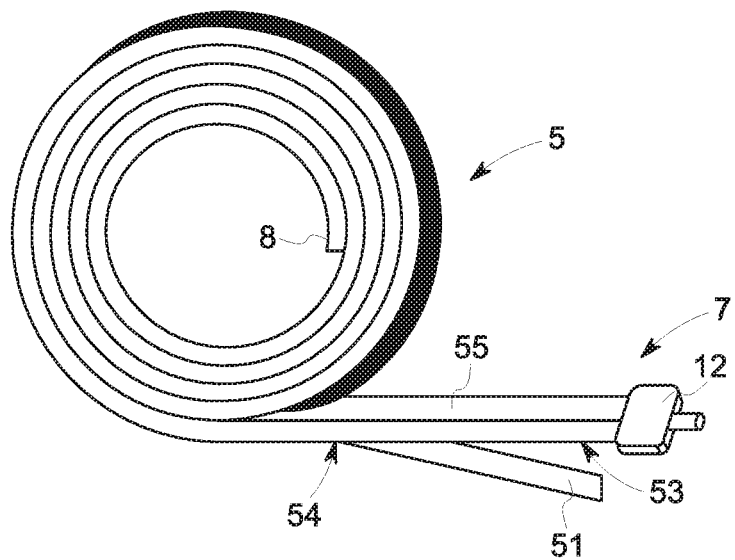
FIG. 2A depicts one embodiment of and adjustable leadwire.

FIG. 2A depicts one exemplary embodiment of an adjustable leadwire 5 in its initial state, prior to fitting the adjustable leadwire 5 to the patient 2. The adjustable leadwire 5 has an initial length between a connector end 7 and a distal end 8. The adjustable leadwire 5 is coiled along its length, and thus the adjustable leadwire 5 is presented in a neat and compact form that can be uncoiled and fitted to the patient 2. The connector end 7 includes connector 12, which may be any connector configured to plug into, or otherwise physically connect with, a receiver 15a associated with ECG monitor 17 (e.g., FIG. 2C). In one embodiment, the adjustable leadwire 5 has a relatively flat formation, with a relatively flat top surface 55 and flat bottom surface 54. In the depicted embodiment, a removable backing 51 covers the bottom surface 54, which has an adhesive 53 thereon. In various embodiments, the adhesive 53 may be along the entire length of the adjustable leadwire 5, or on some portion of the length. The adhesive 53 is preferably positioned to allow the bottom surface 54 of the adjustable leadwire 5 to be adhered to the patient's skin. The removable backing 51 is removed from the adjustable leadwire 5, or from some portion thereof, in order to allow the adhesive 53 to adhere the adjustable leadwire 5 to the patient's skin. A person having ordinary skill in the art will understand in light of this disclosure that the adhesive 53 may be any skin adhesive, several of which are known and available in the relevant art. For instance, the adhesive 53 may be a P-DERM Skin Contact Acrylic Adhesive or Silicone Gel Adhesive by Polymer Science, Inc., or a Silbione Skin Adhesive by Bluestar Silicones International.

Figure 2B:
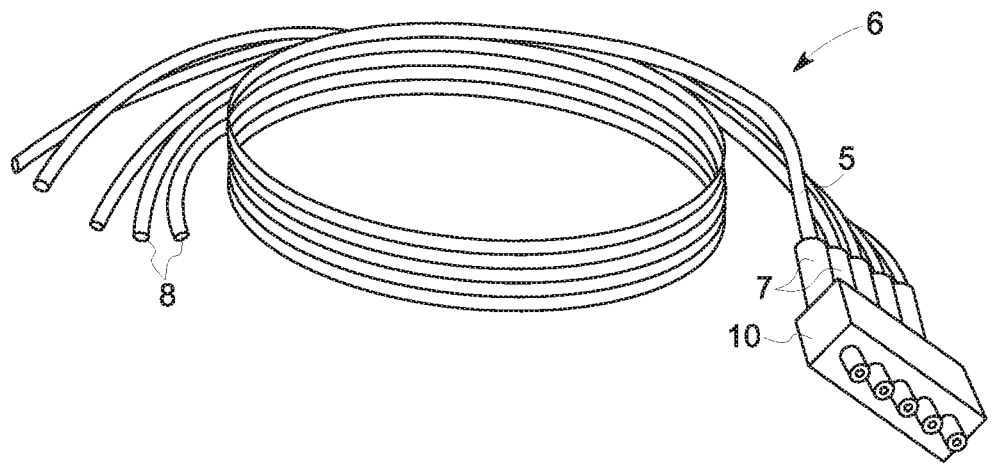
FIG. 2B depicts one embodiment of an adjustable leadwire set.
Figure 2C:
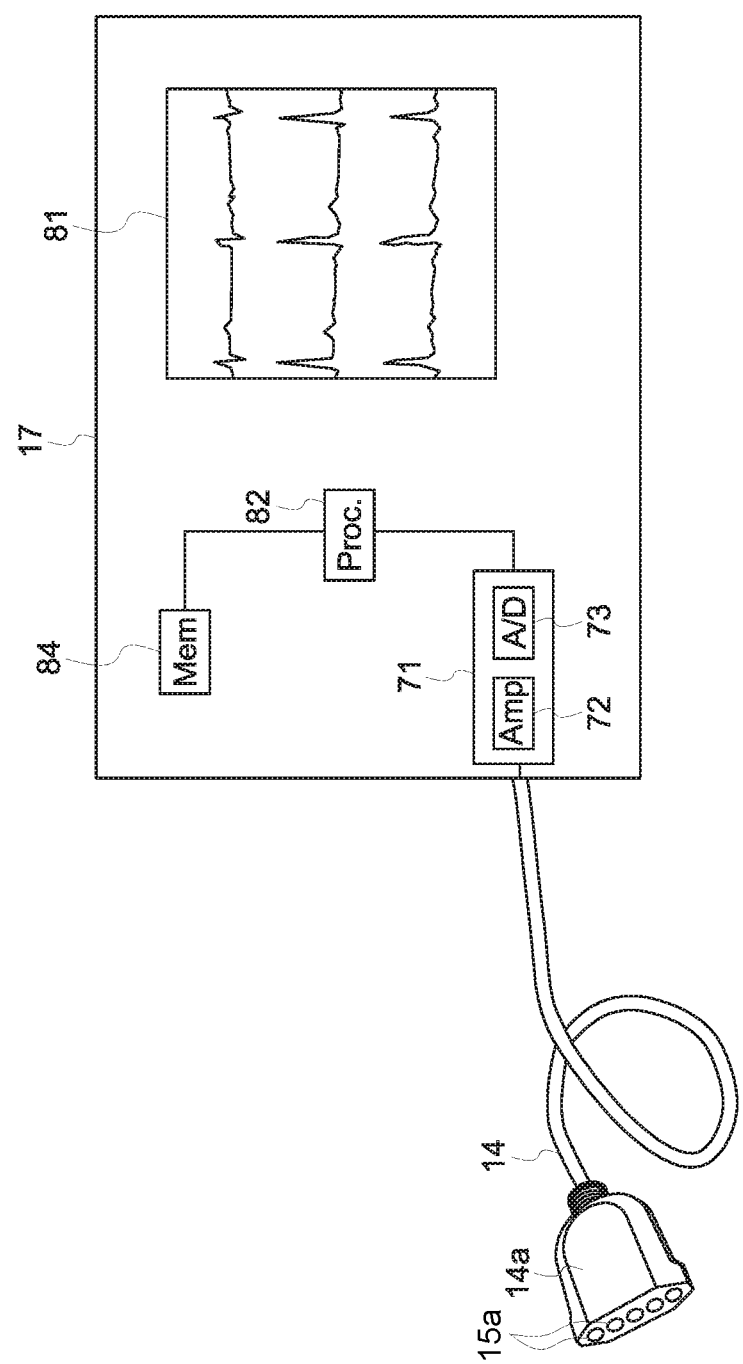
FIG. 2C depicts one embodiment of an ECG monitor having that receives an adjustable leadwire set.

The connector 12 may be any type of connector that provides an electrical connection to a receiver associated with an ECG monitor. FIG. 2C schematically depicts one embodiment of an ECG monitor 17 having a cable 14 providing five receivers 15a capable of receiving connectors 12 from five adjustable leadwires 5. Alternatively, the cable end 14a may be configured to connect to a leadwire set 6, which is a group of adjustable leadwires 5, each having connector ends 7 connected to a common connector 10. In the exemplary embodiment depicted in FIG. 2B, the leadwire set 6 includes five adjustable leadwires 5 configured to be connected to a set of five electrodes 3. In either the single leadwire embodiment exemplified in FIG. 2A or the leadwire set embodiment depicted in FIG. 2B, each adjustable leadwire 5 is sized to a patient by connecting the adjustable leadwire 5 at any point along the length of the adjustable leadwire 5 to an electrode 3. For example, a set of electrodes 3 may be first connected to a patient 2, and then the adjustable leadwires 5 may be sized to accommodate the distance between the connector 12 or common connector 10 and each electrode. Thus, the adjustable leadwire 5 and/or the electrode 3 have a construction that allows an electrical connection to be made between a conductor 57 in the adjustable leadwire 5 and the electrode 3. This can be accomplished in any number of ways. For example, the electrode 3 may be configured to cut through an insulation layer on the adjustable leadwire 5 to connect to the conductor 57 at any point along the length of the adjustable leadwire 5. The electrode 3 may further be configured to sever the adjustable leadwire 5 to eliminate the excess portion and size the adjustable leadwire 5 precisely to the arrangement of electrodes on the patient 2.

Figure 3:
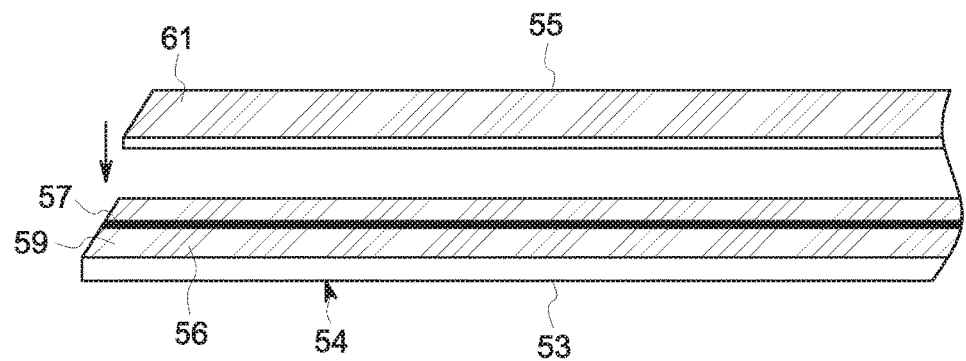
FIG. 3 depicts one embodiment of a portion of an adjustable leadwire

The adjustable leadwires 5 may have any construction that allows for multiple points of connection or connection locations along the length of the adjustable leadwire so that the adjustable leadwire 5 can be fitted to the patient 2. FIG. 3 depicts one embodiment of an adjustable leadwire construction. A flexible substrate 59 has a relatively flat construction with a bottom surface 54 and a top surface 56. The conductor 57 is constructed by printing a conductive material, such as a conductive ink onto the top surface 56 of the flexible substrate 59. Conductive ink is an ink that results in a printed object which conducts electricity. The transformation from liquid ink to solid printing may involve drying, curing or melting processes. These inks allow circuits to be drawn or printed on a variety of substrate materials. These types of inks usually contain conductive materials such as powdered or flaked silver and carbon like materials, although polymeric conduction is also known. As will be understood by a person having ordinary skill in the art in view of this disclosure, a number of conductive inks are available and appropriate for printing a conductive trace onto a flexible substrate to provide a continuous conductor 57 along the length of the adjustable leadwire 5. Other elements may also be printed along the length of the leadwire, such as resistive traces or other circuit elements designed to perform safety or other functions within an ECG leadwire.

The flexible substrate 59 may be comprised of any number of materials. In one embodiment, the flexible substrate 59 is a thermoplastic polyurethane (TPU). Alternatively, the flexible substrate 59 may be a polyethylene terephthalate (PET), or any other plastic material sufficiently flexible to be used as a substrate for composition of the adjustable leadwire 5. An insulating layer 61 is then placed over the top surface 56 of the flexible substrate 59 after the conductor 57 has been printed thereon in order to provide the top surface 55 of the adjustable leadwire 5. The insulating layer 61 may be a separate layer of material that is adhered to the top surface 56 of the flexible substrate 59. For instance, the insulating layer 61 may be comprised of the same material as the flexible substrate 59, such as TPU or PET, or may be any other material that sufficiently insulates the conductor 57 from noise. In another embodiment, the insulating layer 61 may be printed onto the top surface 56 of the flexible substrate 59 and over the conductor 57 in order to shield the conductor 57. For instance, the printed insulated layer 61 may be comprised of Electrodag PF-455B UV-curable insulator paste by Henkel Corporation, or may be 125-17M Screen-printable UV-curable coating by Creative Materials, Inc.

Figure 4A:
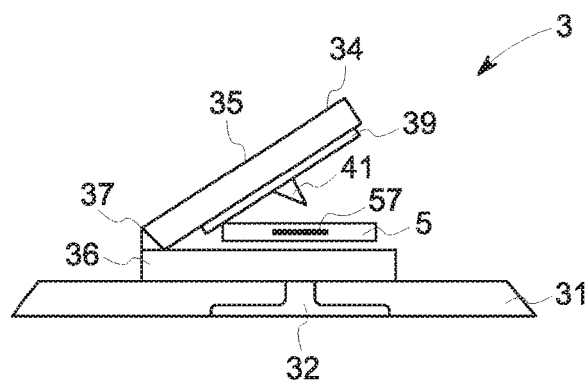
FIG. 4A depicts one embodiment of an electrode connecting to an adjustable leadwire.
Figure 4B:
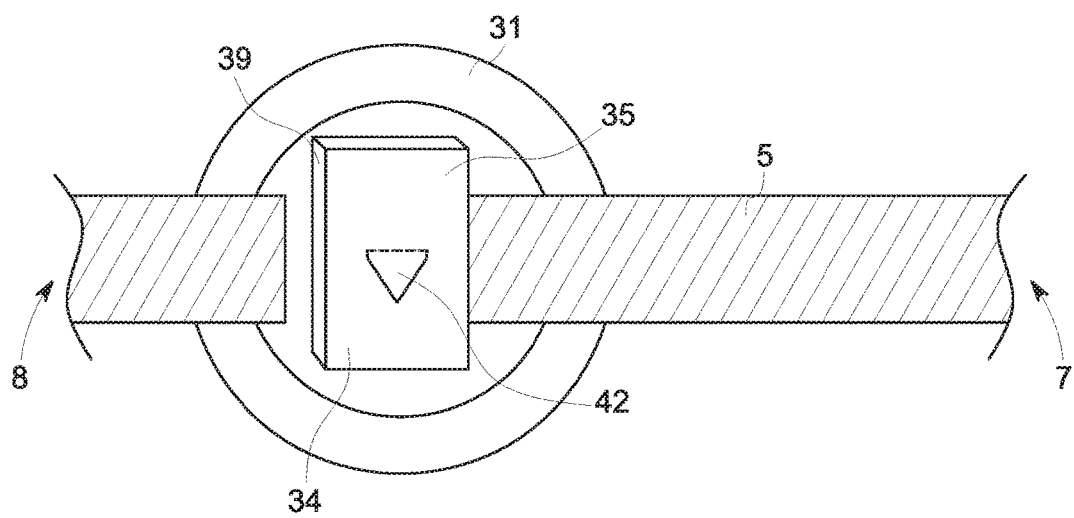
FIG. 4B depicts one embodiment of an electrode connected to an adjustable leadwire to form an adjustable ECG sensor.

FIGS. 4A and 4B depict an exemplary electrode 3 having a clip 34 attachable to the adjustable leadwire 5. Specifically, the clip 34 contains a top portion 35 and a bottom portion 36. The top portion 35 and the bottom portion 36 are connected by hinge 37 that allows the top portion 35 to move, and specifically to open and close, with respect to the bottom portion 36. The clip 34 can be opened to receive the adjustable leadwire 5, and then closed to attach to any of multiple locations along the length of the adjustable leadwire 5, which may be designated locations or any where along the length. For example, the clip 34 may attach to the adjustable leadwire 5 by clasping or otherwise closing onto indentations or marked portions of the flexible substrate 59.

The electrode 3 further includes a pin 41 capable of puncturing the adjustable leadwire 5 in order to electrically connect to the conductor 57 in the adjustable leadwire 5. The pin 41 is made of metal or some conductive material and is configured to puncture at any of multiple locations along the length of the leadwire 5, which may be designated locations or any where along the length. For example, the adjustable leadwire 5 may have perforated portions, or portions that are otherwise configured to be punctured by the pin 41. The pin 41 may take on any form allowing connection to the conductor 57, such as a pointed portion that punctures the insulator 61 and/or flexible substrate 59 upon application of pressure. In one embodiment, the electrode 3 is configured such that closing the clip 34 on the adjustable leadwire 5 applies the pressure necessary to cause the pin 41 to contact the conductor 57.

The electrode 3 further includes a blade 39 such that when the clip 34 is closed to attach to the adjustable leadwire, the blade 39 cuts the adjustable leadwire 5, severing it at a location between the distal end 8 and the connection point between the pin 41 and the conductor 57. Further, in the embodiment depicted in FIG. 4A, the clip 34 also includes the pin 41. Accordingly, when the clip 34 closes on the adjustable leadwire 5, the pin 41 punctures the flexible substrate 59 and/or insulating top layer 61 of the adjustable leadwire 5 to electrically connect to the conductor 57. Cardiac signals, or potentials, are conducted through the patient's skin to the conductive portion 32 of the electrode 3, and from the conductive portion 32 to the bottom portion 36 of the clip 34.

In the depicted embodiment, the pin 41 and the blade 39 are both on the top portion 35 of the clip 34. However, in other embodiments the pin 41 and/or the blade 39 may be on the bottom portion 36 of the clip 34. In either embodiment, closing the clip 34 forces the pin 41 and blade 39 through the flexible substrate 59 and/or the insulating top layer 61. In one embodiment depicted in FIGS. 4A and 4B, the clip 34 is made of metal and the top portion 35 of the clip has a triangular-shaped cutout 42 that is pushed downward to form the pin 41.

The pin 41 electrically connects to the conductive portion 32 of the electrode 3. For example, the pin 41 may be positioned on the clip 34 such that it contacts the conductive portion 32 when the clip 34 is in the closed position. Thereby, the cardiac signals are transmitted through the conductive portion 32, to the pin 41, and then to the conductor 57 of the adjustable leadwire 5. For example, the conductive portion 32 may be a metal conductor and/or may include a gel-soaked sponge in contact with the patient's skin. In addition to the conductive portion 32, the electrode pad 31 may also include an adhesive portion that adheres the conductive portion 32 to the patient's skin, such as a foam pad with an adhesive on one side. Alternatively, the clip 34 is conductive, such as made of metal, and the cardiac signals from the conductive portion 32 are conducted through the metal clip 34, into the pin 41, and into the conductor 57 of the adjustable wire 5.

In various embodiments, the adjustable leadwire 5 may make a physical electrical connection to a receiver associated with an ECG monitor 17, or may wirelessly connect to a wireless receiver associated with an ECG monitor 17. FIG. 2C depicts an embodiment having a cable 14 providing one or more receivers 15*a*, or receptacles, that each electrically connect to a connector 12 of an adjustable leadwire 5 or a common connector 10 of multiple adjustable leadwires 5. The cardiac signals are conducted from the conductor 57 of the adjustable leadwire 5 through the connection between the connector 10, 12 and cable 14 to the ECG monitor 17. The cardiac signals are received at a signal processing module 71, which includes one or more amplifiers 72 and analog-to-digital (A/D) converters 73. The amplified and digitized cardiac signals from the various adjustable ECG sensors 1 are processed by processor 82, such as by execution of software stored in memory 84 by the processor 82, resulting ECG waveforms that may be displayed on a display 81 associated with the ECG monitor 17.

Figure 5:
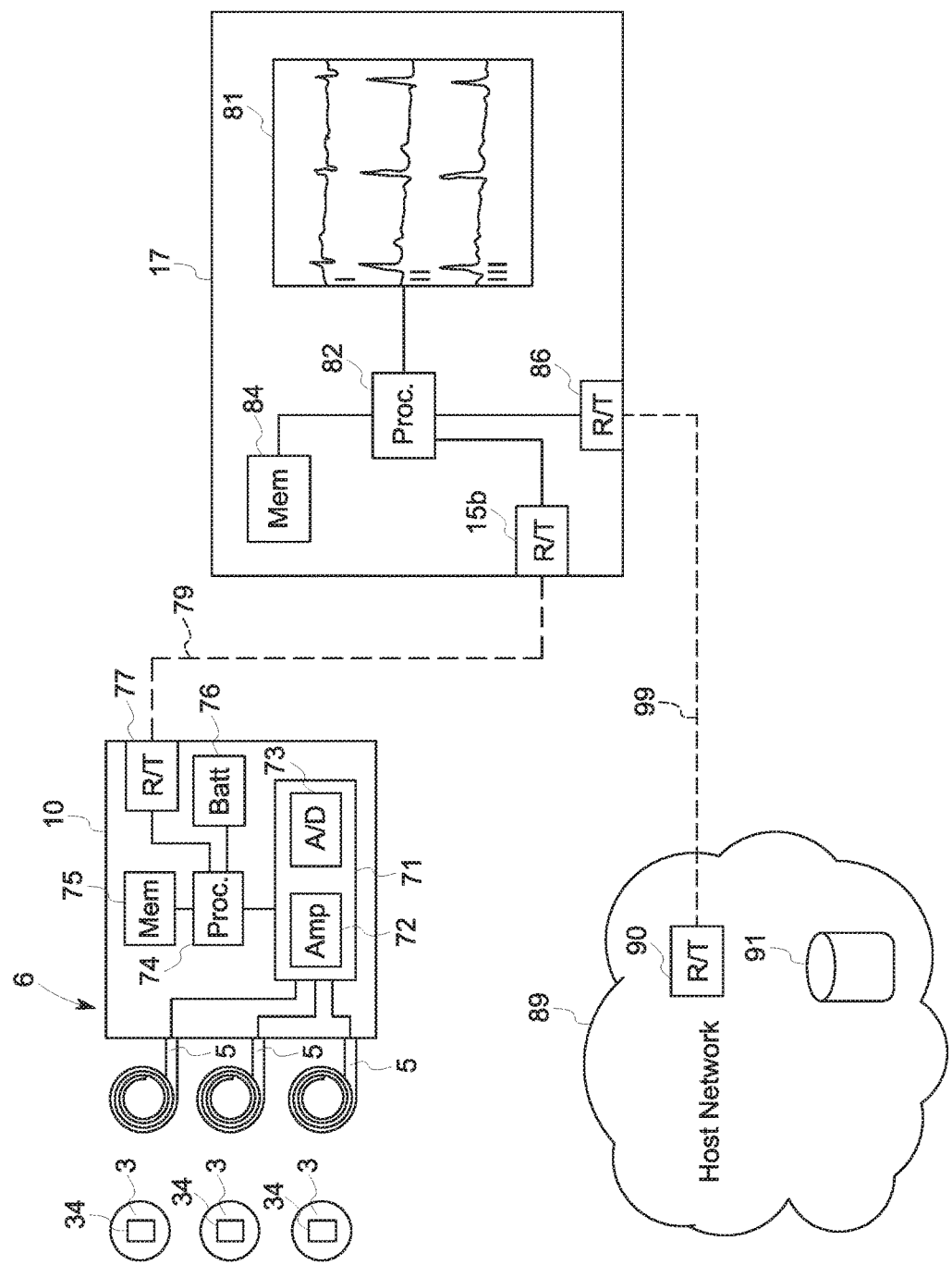
FIG. 5 depicts one embodiment of an ECG monitoring system incorporating an adjustable leadwire set.

FIG. 5 depicts an exemplary embodiment of a wireless ECG monitoring system incorporating a leadwire set 6 having a common connector 10 wirelessly connected to wireless receiver 15b, which in the depicted embodiment is a receiver/transmitter or transceiver. The depicted the common connector 10 includes signal processing module 71 having one or more amplifiers 72 and A/D converters 73 sufficient to amplify and digitize the cardiac signals received through each of the adjustable leadwires 5 in the leadwire set 6. For example, a leadwire set 6 having ten adjustable leadwires 5 (and thus configured to connect to ten electrodes 3) may be is configured so that one adjustable leadwire 5 is connected to a ground or reference electrode 3 and the remaining 9 electrodes are used to as inputs to eight amplifiers 72 and are digitized by eight A/D converters 73 to generate signals from which a standard 12-lead ECG is derived. As will be understood by a person having ordinary skill in the art in view of this disclosure, the leadwire set 6 may incorporate any number of adjustable leadwires 5, such as 3, 5, 10, or some number associated with a known electrode configuration for ECG monitoring.

The amplified and digitized cardiac signals are outputted from the signal processing module 71 and then transmitted to the ECG monitor 17. In the depicted embodiment, the common connector 10 includes processor 74 that executes software stored in memory 75 in order to control receiver transmitter 77 to transmit the amplified and digitized cardiac signals to the ECG monitor 17. Specifically, receiver transmitter 77 of the common connector 10 communicates with receiver transmitter 15b of the ECG monitor 17 via communication link 79, which may be by any of various available wireless communication protocols. For example, communication link 79 may be according to any relatively short-range radio protocol, such as Bluetooth low energy (BLE), ANT, ZigBee, or Nearfield Communication (NFC). In other embodiments, the communication link 79 may be via network protocols appropriate for longer range wireless transmissions, such as on the wireless medical telemetry service (WMTS) spectrum, or on a Wi-Fi-compliant wireless local area network (WLAN). The common connector 10 further includes a battery 76 to power the processor 74, signal processing module 71, and receiver transmitter 77.

The ECG monitor 17 may be connected to a host network 89, such as by wireless means, as exemplified in FIG. 5. ECG monitor 17 may further include a second receiver transmitter 86 in wireless communication with a receiver transmitter 90 of a host network 89, such as a hospital computer network or a cloud-hosted computer network. The host network 89 may store the ECG waveforms or other cardiac information received from the ECG monitor 17 in a database 91 such as a patient medical record database and/or a database of cardiac waveforms, such as a MUSE ECG management system available by General Electric Company. The communication link 99 may be via any known network protocol, such as on the WMTS spectrum, a WLAN, or other network protocols appropriate for longer range wireless transmission.

In a preferred embodiment, the adjustable leadwires 5 are disposable elements intended for single-use on a patient 2. In various embodiments, the connectors 10, 12 at the connector ends 7 of the adjustable leadwires 5 may be disposable or reusable. For example, the common connector 10 may be a disposable device supplied with and inseparable from the disposable adjustable leadwires 5. In another embodiment, the common connector 10 may be reusable, in which case the adjustable leadwires 5 may have connectors 12 at the connection ends 7 configured to be plugged into or otherwise attached to corresponding receiver ports in the common connector 10.

In another embodiment, the processor 74, memory 75, battery 76, and radio transmitter 77 may be in a separate device connectable via a dedicated connector to the signal processing module 71 and leadwires 5. In such an embodiment, the device portion containing the processor 74 etc. may be reusable, while the device portion having the leadwires 5 and the signal processing module 71 may be disposable.

Figure 6:
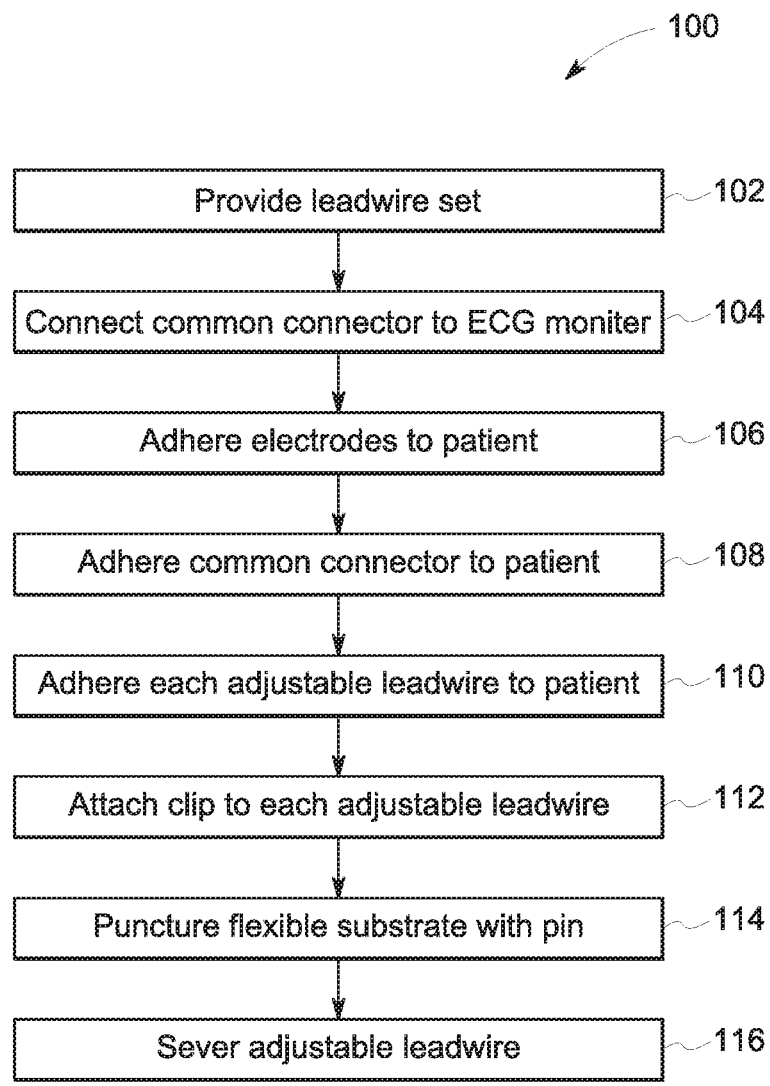
FIG. 6 is a flowchart depicting one embodiment of a method of fitting an adjustable ECG sensor to a patient.

FIG. 6 depicts one embodiment of a method 100 of fitting an adjustable ECG sensor 1 to a patient 2. A leadwire set 6 including multiple adjustable leadwires 5 is provided at step 102. Alternatively, multiple individual adjustable leadwires 5 may be provided, or accessed, as described above. The common connector 10 of the leadwire set 6 is connected to the ECG monitor 17 at step 104. As described herein, such connection may be by wired or wireless means. A set of electrodes 3 are adhered to the patient according to a prescribed electrode configuration. The common connector is adhered to the patient at step 108, such as to a location on the patient's torso. Each adjustable leadwire is then adhered to the patient at step 110, such as by unrolling the length of adjustable leadwire 5 and removing the removable backing 51 from the bottom surface 54 of the flexible substrate 59 in order to reveal the adhesive 53. Each adjustable leadwire 5 in the leadwire set 6 is run to one of the electrodes 3. Each adjustable leadwire 5 is connected to an electrode 3 by attaching the clip 34 of the electrode 3 to the adjustable leadwire 5 at step 112. At step 114, the pin 41 punctures the flexible substrate 59 in order to form a connection point with the conductor 57. The adjustable leadwire is severed at step 116 between the distal end 8 and the connection point in order to remove the excess adjustable leadwire, thereby sizing the adjustable leadwire 5 from its initial length to an exact length necessary for the particular ECG sensing arrangement on the patient 2.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. An adjustable ECG sensor attachable to a patient to sense cardiac signals, the adjustable ECG sensor comprising:
    an adjustable leadwire having a connector end connectable to a receiver associated with an ECG monitor;
    an electrode having:
    an electrode pad;
    a clip connected to the electrode pad and attachable to any one of multiple locations on the adjustable leadwire;
    a pin connected to the clip that punctures and electrically connects to the adjustable leadwire; and wherein the adjustable ECG sensor is fitted to the patient by attaching the clip of the electrode to one of the multiple locations on the adjustable leadwire.

2. The adjustable ECG sensor of claim 1, further comprising a blade on the clip of the electrode, the blade positioned to sever the adjustable leadwire when the clip attaches to the any one of multiple locations on the adjustable leadwire.

3. The adjustable ECG sensor of claim 1, wherein the pin is incorporated into the clip such that the adjustable leadwire is punctured when the clip is attached to the any one of multiple locations on the adjustable leadwire.

4. The adjustable ECG sensor of claim 1, further comprising:
    wherein the adjustable leadwire comprises a conductor extending along a flexible substrate; and
    an adhesive on one side of the flexible substrate and configured to adhere the flexible substrate to a patient's skin; and
    wherein the pin punctures the flexible substrate and contacts the conductor.

5. The adjustable ECG sensor of claim 4, wherein the flexible substrate has a flat top surface and a flat bottom surface, wherein the adhesive is on the flat bottom surface.

6. The adjustable ECG sensor of claim 5, wherein the conductor is formed by conductive ink printed on the flat top surface of the flexible substrate.

7. The adjustable ECG sensor of claim 6, wherein the flexible substrate is thermoplastic polyurethane (TPU).

8. The adjustable ECG sensor of claim 6, wherein the adjustable leadwire further includes an insulating layer over the top surface of the flexible substrate and the conductor.

9. The adjustable ECG sensor of claim 1, wherein the connector end includes a connector that plugs into the receiver associated with the ECG monitor.

10. The adjustable ECG sensor of claim 1, wherein the receiver associated with the ECG monitor is a wireless receiver, and the connector end includes a wireless transmitter that wirelessly connects to the wireless receiver to wirelessly transmit the cardiac signals to the ECG monitor.

11. The adjustable ECG sensor of claim 10, wherein the adjustable leadwire is part of a leadwire set sharing a common connector containing the wireless transmitter, where the connector end of each adjustable leadwire in the leadwire set is connected to the common connector.

12. A method of fitting an adjustable ECG sensor to a patient to sense cardiac signals, the method comprising:
    adhering an electrode to a patient, the electrode having an electrode pad, a clip connected to the electrode pad, and a pin connected to the clip;
    fitting an adjustable leadwire to the patient, the adjustable leadwire having an initial length of a flexible substrate having a connector end and a distal end, a conductor extending along the flexible substrate, and an adhesive on one side of the flexible substrate, by:
        adhering the adjustable leadwire to the patient's skin;
        attaching the clip to any one of multiple locations on the adjustable leadwire;
        puncturing the flexible substrate with the pin to electrically connect to the conductor of the adjustable leadwire at a connection point; and
        severing the adjustable leadwire between the distal end and the connection point.

13. The method of claim 12, wherein the clip on the electrode includes a blade, and wherein the step of severing the adjustable leadwire is performed when the clip is attached to the any one of multiple locations on the adjustable leadwire.

14. The method of claim 12, wherein the pin is incorporated into the clip such that the step of puncturing the flexible substrate is performed when the clip is attached to the any one of multiple locations on the adjustable leadwire.

15. The method of claim 12, further comprising connecting a connector of the connector end of the adjustable leadwire to a receiver associated with an ECG monitor.

* * * * *